US012601728B2

(12) United States Patent
Mooshammer et al.

(10) Patent No.: US 12,601,728 B2
(45) Date of Patent: Apr. 14, 2026

(54) PRECISION FARMING SYSTEM WITH SCALED SOIL CHARACTERISTICS

(71) Applicant: MIRATERRA INC., Lewes, DE (US)

(72) Inventors: Maria Mooshammer, El Cerrito, CA (US); Sheng-Yang Matthew Goh, San Francisco, CA (US); David C. Stone, San Francisco, CA (US); Tyler Barnum, Redwood City, CA (US); Patrick L. Dumstorff, Chicago, IL (US); Ronald O. Zink, Mercer Island, WA (US); Poornima Parameswaran, Menlo Park, CA (US)

(73) Assignee: MIRATERRA INC., Lewes, DE (US)

( * ) Notice: Subject to any disclaimer, the term of this patent is extended or adjusted under 35 U.S.C. 154(b) by 0 days.

(21) Appl. No.: 18/398,750

(22) Filed: Dec. 28, 2023

(65) Prior Publication Data

US 2024/0125758 A1     Apr. 18, 2024

Related U.S. Application Data

(62) Division of application No. 17/677,403, filed on Feb. 22, 2022, now Pat. No. 11,899,006.

(51) Int. Cl.
*G01N 33/24*          (2006.01)
*A01B 79/00*         (2006.01)

(52) U.S. Cl.
CPC ........... *G01N 33/24* (2013.01); *A01B 79/005* (2013.01); *G01N 33/243* (2024.05); *G01N 33/245* (2024.05)

(58) Field of Classification Search
CPC ............. G01N 33/24; G01N 2033/243; G01N 2033/245; A01B 79/005
See application file for complete search history.

(56) References Cited

U.S. PATENT DOCUMENTS

| | | | |
|---|---|---|---|
| 10,762,982 B1 | 9/2020 | Wu et al. | |
| 11,385,215 B2 * | 7/2022 | Hartman | ................ G16B 20/00 |
| 11,899,006 B2 * | 2/2024 | Mooshammer | ...... A01B 79/005 |
| 2015/0284810 A1 | 10/2015 | Knight et al. | |
| 2017/0090006 A1 | 3/2017 | Kumar et al. | |
| 2017/0090068 A1 | 3/2017 | Xiang et al. | |
| 2019/0227046 A1 | 7/2019 | Parameswaran et al. | |
| 2020/0005166 A1 | 1/2020 | Reich et al. | |
| 2021/0112705 A1 | 4/2021 | Coolidge et al. | |
| 2022/0189588 A1 | 6/2022 | Song et al. | |

(Continued)

FOREIGN PATENT DOCUMENTS

| | | | |
|---|---|---|---|
| JP | 2016180599 A | * | 10/2016 |
| WO | 2016000072 A1 | | 1/2016 |

OTHER PUBLICATIONS

JP-2016180599-A, English Translation (Year: 2016).*

(Continued)

*Primary Examiner* — Ryan D Walsh
(74) *Attorney, Agent, or Firm* — FBT Gibbons LLP

(57) ABSTRACT

A method of indicating a characteristic of a soil sample of a field includes measuring a co-factor in the soil sample and using the co-factor to place the soil sample in a soil sample group. The characteristic of the soil sample is measured and then is scaled based on the soil sample group. The scaled measure is displayed to better represent the characteristic of the soil sample relative to soil samples of the sample group.

12 Claims, 12 Drawing Sheets

(56) References Cited

U.S. PATENT DOCUMENTS

2023/0123300 A1   4/2023   McGlade et al.
2023/0266295 A1   8/2023   Mooshammer et al.

OTHER PUBLICATIONS

Andrews et al., The soil management assessment framework: A quantitative soil quality evaluation method, Soil Science Society of America Journal, vol. 68, pp. 1945-1962, 2004.
Dari et al., Consistency of the threshold phosphorus saturation ratio across a wide geographic range of acid soils, Agrosystems, Geosciences & Environment, vol. 1, pp. 1-8, 2018.
Devine et al., A regional soil classification framework to improve soil health diagnosis and management, Soil Science of Society of America Journal, vol. 85.2, pp. 361-378, 2021.
Fine et al., Statistics, scoring functions, and regional analysis of a comprehensive soil health database, Soil Science Society of America Journal, vol. 81, pp. 589-601, 2017.
Nair et al., A capacity factor as an alternative to soil test phosphorus in phosphorus risk assessments, New Zealand Journal of Agricultural Research, vol. 47, Issue 4, pp. 491-497, 2004.
Sims et al., Evaluation of Mehlich 3 as an Agri-Environmental Soil Phosphorus Test for the Mid-Atlantic, United States of America, Soil Science Society of America Journal, vol. 66, pp. 2016-2032, 2002.
Prosecution history of corresponding U.S. Appl. No. 17/677,403 including: Notice of Allowanced dated Oct. 2, 2023, Amendment dated Sep. 13, 2023 and Office Action dated Jun. 13, 2023, 25 pages.

* cited by examiner

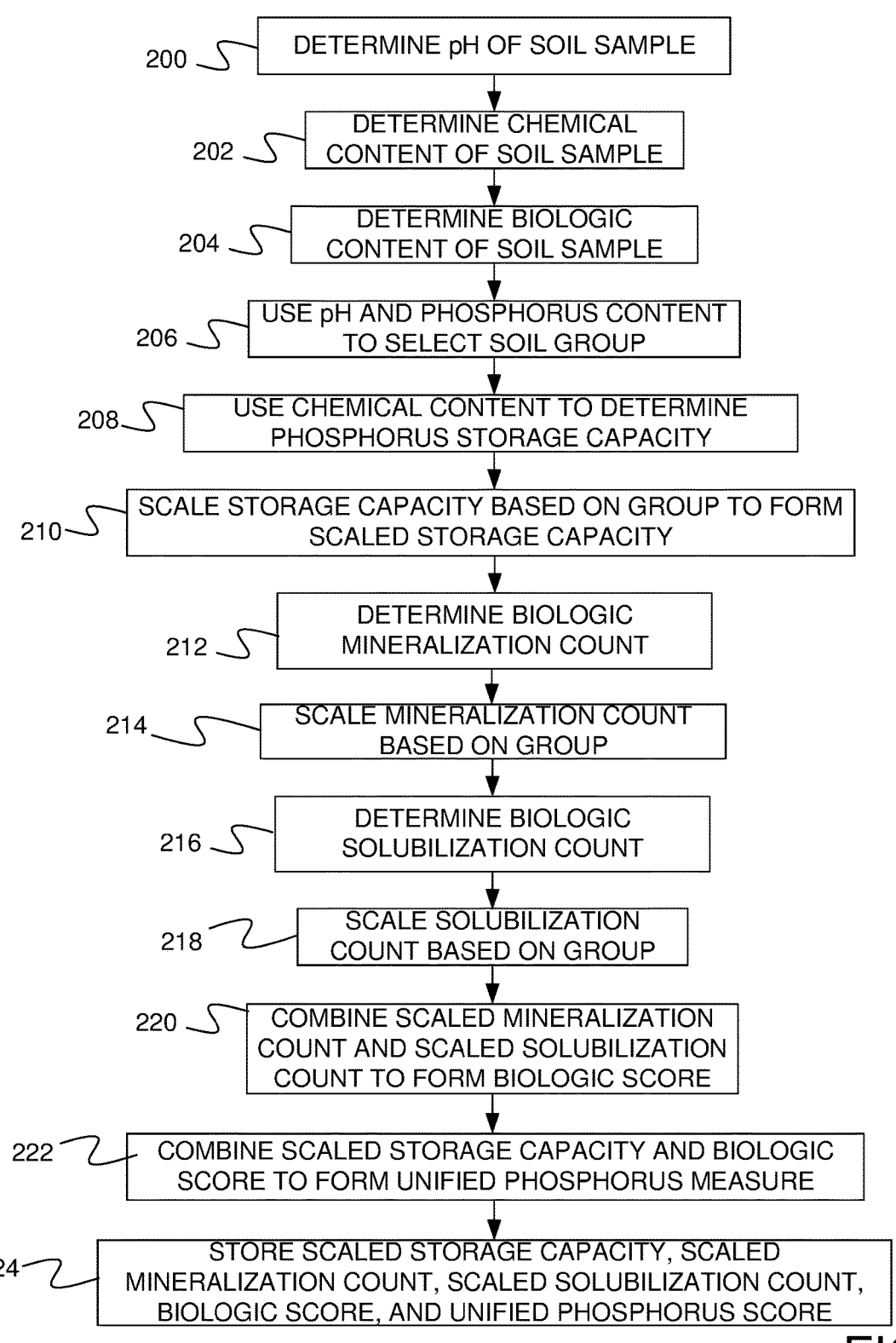

200 — DETERMINE pH OF SOIL SAMPLE

202 — DETERMINE CHEMICAL CONTENT OF SOIL SAMPLE

204 — DETERMINE BIOLOGIC CONTENT OF SOIL SAMPLE

206 — USE pH AND PHOSPHORUS CONTENT TO SELECT SOIL GROUP

208 — USE CHEMICAL CONTENT TO DETERMINE PHOSPHORUS STORAGE CAPACITY

210 — SCALE STORAGE CAPACITY BASED ON GROUP TO FORM SCALED STORAGE CAPACITY

212 — DETERMINE BIOLOGIC MINERALIZATION COUNT

214 — SCALE MINERALIZATION COUNT BASED ON GROUP

216 — DETERMINE BIOLOGIC SOLUBILIZATION COUNT

218 — SCALE SOLUBILIZATION COUNT BASED ON GROUP

220 — COMBINE SCALED MINERALIZATION COUNT AND SCALED SOLUBILIZATION COUNT TO FORM BIOLOGIC SCORE

222 — COMBINE SCALED STORAGE CAPACITY AND BIOLOGIC SCORE TO FORM UNIFIED PHOSPHORUS MEASURE

224 — STORE SCALED STORAGE CAPACITY, SCALED MINERALIZATION COUNT, SCALED SOLUBILIZATION COUNT, BIOLOGIC SCORE, AND UNIFIED PHOSPHORUS SCORE

FIG. 2

PRECISION FARMING SYSTEM WITH SCALED SOIL CHARACTERISTICS

CROSS-REFERENCE TO RELATED APPLICATION

The present application is a divisional of and claims priority of U.S. patent application Ser. No. 17/677,403, filed Feb. 22, 2022, the content of which is hereby incorporated by reference in its entirety.

BACKGROUND

Precision farming systems divide fields into zones, determine the current conditions in each zone and report those conditions to farmers so that the farmer can decide what actions to take in each zone. Example conditions include nutrient levels, such as nitrogen and phosphorus levels, organic matter levels and moisture levels.

The discussion above is merely provided for general background information and is not intended to be used as an aid in determining the scope of the claimed subject matter. The claimed subject matter is not limited to implementations that solve any or all disadvantages noted in the background.

SUMMARY

A method of indicating a characteristic of a soil sample of a field includes measuring a co-factor in the soil sample and using the co-factor to place the soil sample in a soil sample group. The characteristic of the soil sample is measured and then is scaled based on the soil sample group. The scaled measure is displayed to better represent the characteristic of the soil sample relative to soil samples of the sample group.

In accordance with a further embodiment, a method includes using a pH of a soil sample to select a group of soil samples. A characteristic of the soil sample is measured to produce a measured value then the measured value is scaled based on measured values determined for soil samples in the group of soil samples to form a scaled value. The scaled value is displayed instead of the measured value so as to improve a precision farming system.

In accordance with a still further embodiment, a method includes using a pH level and a phosphorus level of a soil sample to select a sample group for the soil sample. A measure of phosphorus storage capacity of the soil sample is determined relative to soil samples in the sample group and a user interface depicting the measure of the phosphorus storage capacity is displayed.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 2 is a flow diagram of a method of processing a soil sample using the system of FIG. 1.

DETAILED DESCRIPTION

Figure 1:
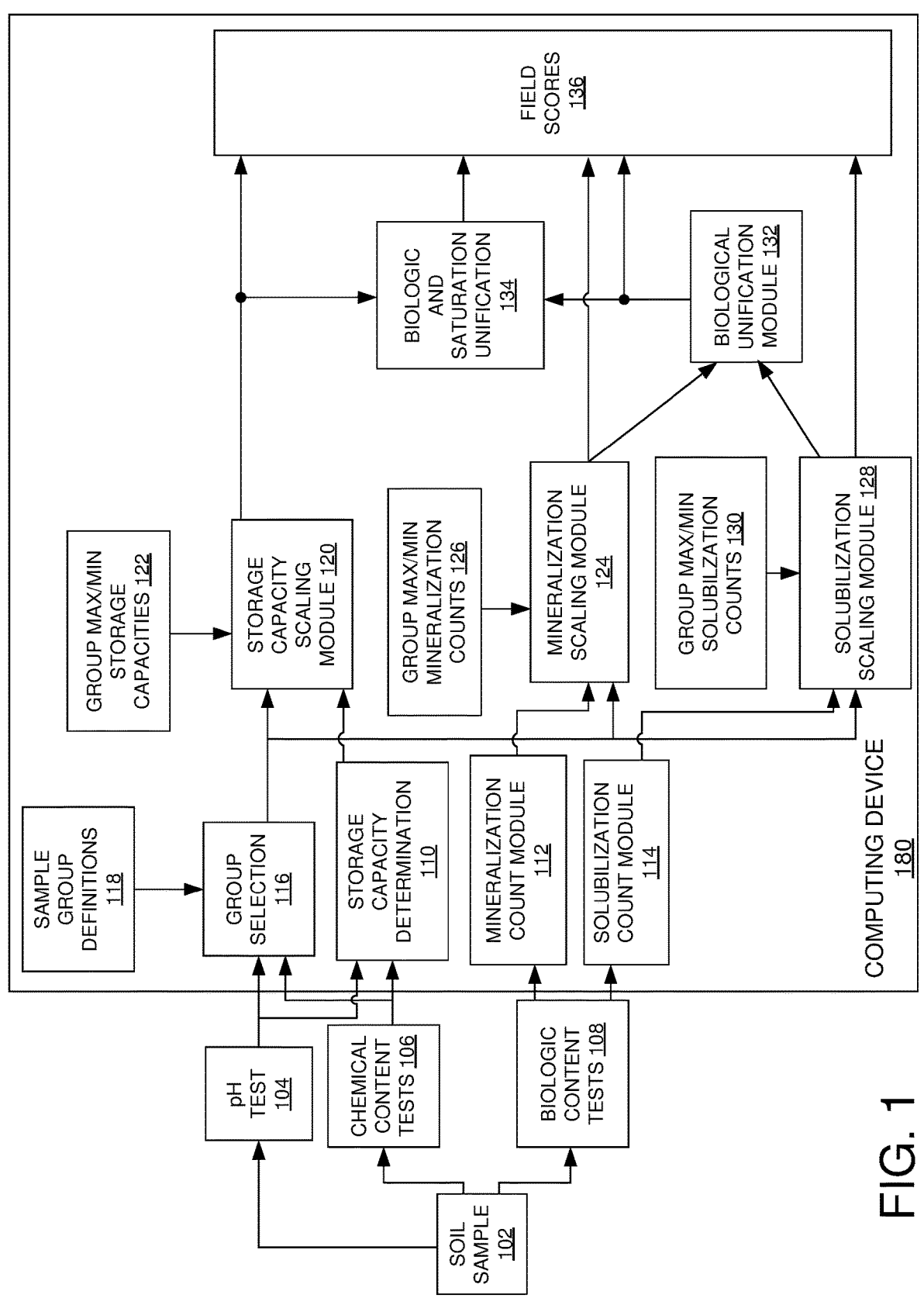
FIG. 1 is a block diagram of a system for generating a unified phosphorus score for a soil sample.

Prior art precision farming systems are difficult for farmers to use because the user interfaces return confusing nutrient information that does not by itself indicate whether the farmer should take action to try to improve yields. Specifically, under the prior art, it is possible for two fields, one needing treatment and one not needing treatment, to generate the same nutrient value. It is not that prior art precision farming systems are incorrectly measuring the nutrient value in the field. Instead, the present inventors have discovered that prior art precision farming systems erroneously assume that every zone in every field can achieve the maximum nutrient value possible in any field anywhere. The present inventors have discovered that this is not true and have further discovered certain co-factors that allow samples to be grouped together to define attainable nutrient value ranges for a field. By using these ranges of attainable values, the embodiments described below improve precision farming systems by providing nutrient information that is less confusing to farmers. Specifically, in the embodiments below, the nutrient values returned to the farmer are directly indicative of the degree to which the yield in the zone can be improved since the nutrient values are scaled relative to nutrient values of other zones in the sample group. This allows the farmer to quickly assess whether they should take action to improve some aspect of the field.

The co-factors that have been identified are characteristics of the soil samples that allow the soil samples to be grouped. In particular, the co-factors form groups of soil samples that each have smaller ranges of values for the nutrient values of interest than the range provided by the all of the soil samples. In accordance with one embodiment, some of the smaller ranges overlap parts of the smaller ranges of other sample groups. Others of the smaller ranges do not overlap any other sample group's range of nutrient values.

One example of nutrient values produced by the present embodiments are values related to phosphorus availability in a zone. Specifically, nutrient values representing: phosphorus storage capacity, phosphorus solubilization potential and phosphorus mineralization potential. Phosphorus storage capacity is a measure of the degree to which phosphorus can be added to the zone before the zone is saturated. Once a zone reaches a saturation level, any additional phosphorus will either runoff or leach out of the soil. Phosphorus solubilization potential and phosphorus mineralization potential provide measures of the ability of microbes in the soil to convert phosphorus from a form that is not usable by plants to one that is usable. Specifically, phosphorus solubilization potential is a measure of the ability to convert phosphorus from an unusable insoluble form to a usable soluble form while phosphorus mineralization potential is a measure of the ability to convert phosphorus from an unusable organic form to a usable inorganic form.

Under prior art precision farming systems, when phosphorus storage capacity, phosphorus solubilization potential or phosphorus mineralization potential are determined, it is assumed that every zone in every field can achieve the maximum phosphorus storage capacity, maximum phosphorus solubilization potential and maximum phosphorus mineralization potential of any field in the world. The present inventors have discovered that this is not true and that for any given zone, the attainable values for these measures are limited to respective ranges. The inventors have further discovered that co-factors, such as pH and phosphorus content, can be used to group samples so as to define these ranges for each sample. Thus, within a group of samples, the present embodiments are able to set a respective maximum value and a respective minimum value for each of the phosphorus storage capacity, phosphorus solubilization potential and phosphorus mineralization potential. Because these ranges better reflect what is attainable for the zone that a sample was taken from, the resulting values returned to the farmer more clearly indicate whether the yield of the zone could be improved with treatment.

FIG. 1 provides a block diagram of a system 100 for generating phosphorus availability values for a soil sample. FIG. 2 provides a method of processing a soil sample using system 100.

In step 200, a portion of a soil sample 102 is subject to a pH test 104 to determine the pH of the soil. At step 202, a portion of soil sample 102 is subject to chemical content tests 106 to determine the chemical content of soil sample 102 including the amount of various elements and chemical compounds in soil sample 102. In accordance with one embodiment, chemical content tests 106 determine an amount of phosphorus, aluminum, and calcium in soil sample 102. In step 204, a portion of soil sample 102 is applied to biologic content tests 108 to determine the biologic content of the soil sample. In particular, biologic content tests 108 isolate genetic sequences of microbes in soil sample 102 so that various genetic sequences can be counted.

Figure 3:
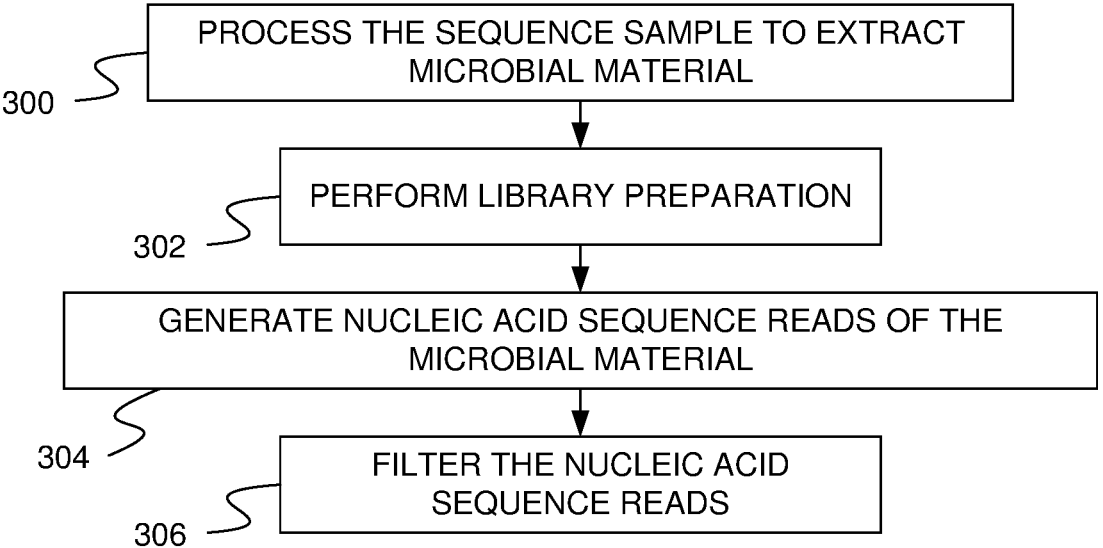
FIG. 3 is a flow diagram of a method of performing biologic content tests.

FIG. 3 provides a flow diagram of a method of performing biologic content tests 108. Soil sample 102 is processed at step 300 to extract microbial material (also referred to as microbial genetic material). In some embodiments, soil sample 102 may be stored at −80 degrees Celsius prior to extraction of the microbial material. In accordance with one embodiment, soil sample 102 is added to extraction vessels by mass, volume, suspension volume, or another measurement. Cell lysis is performed on the soil sample to release the microbial material including intracellular nucleic acids. Cell lysis may include chemical (buffers or salts), mechanical (bead beating or sonication), or thermal (e.g., freezing, free-thaw cycling, or microwaving) processes. Soil and released microbial material are separated. Cellular debris may be removed using chemical precipitation or centrifugation. Additionally, contaminants may be removed using precipitation and elution of the microbial material. The microbial material may be prepared using fluorescent dyes or gels for downstream assay or spectroscopy.

In some embodiments, the nucleic acids of the microbial material may be processed prior to library preparation. For example, target genes or genome regions may be enriched for polymerase chain reaction (PCR) amplification or amplicon sequencing. Targeted DNA primers may be used to flank a region of interest. In some use cases, DNA fragment size may be controlled chemically using size selection gel beads, physically using ultrasonic shearing, or enzymatically using transposase fragmentation.

At step 302 sequencing library preparation is performed on the extracted microbial material. Library preparation may include attaching sequencing adapters or tags to nucleic acids to facilitate reading of the nucleic acids. Sequencing tags may be unique to each sample (e.g., serving as a barcode) and enable identification of sequenced data associated with each sample in a multiplexed run with multiple samples. Libraries may also be prepared using other suitable methods such as ligation or transposase. In some use cases, library preparation includes protocols from sequencer original equipment manufacturers (OEMs), third party kit providers, or other resources.

Once the sequencing library is prepared, the library or a portion of the library can be sequenced such that nucleic acid sequence reads of the microbial material are generated at step 304 using one or more techniques. In some embodiments, a sequencer performs sequencing (e.g., of DNA or RNA) and outputs sequence reads of the microbial material. In some embodiments, the nucleic acid sequence reads are generated using next generation sequencing (NGS) techniques including synthesis technology (ILLUMINA®), pyrosequencing (454 LIFE SCIENCES), ion semiconductor technology (Ion Torrent sequencing), single-molecule real-time sequencing (PACIFIC BIOSCIENCES®), or nanopore sequencing (OXFORD NANOPORE TECHNOLOGIES). DNA sequencing can also be performed as described in Sanger et al. (PNAS 74:5463, (1977)) and the Amersham International plc sequencing handbook, which methods are incorporated by reference herein.

At step 306, the nucleic acid sequence reads are filtered. For example, low quality sequence reads are discarded. Sequence reads can be considered of low quality by determining that a length of the sequence read is less than a threshold value, the sequence read includes at least a threshold number of ambiguous bases, or a read quality score (e.g., determined using a third-party tool) is less than a threshold score, for example.

Returning to FIG. 2, at step 206, the pH determined by pH test 104 and the phosphorus content of the soil sample determined by chemical content tests 106 are provided to a group selection module 116 executed by a processor (not shown) in a computing device 180. Group selection module 116 uses the pH and the phosphorus content to select a sample group for soil sample 102. In accordance with one embodiment, each sample group is defined as samples that have homogeneous characteristics based on multiple co-factors.

At step 208, a phosphorus saturation determination module 110 uses the chemical content of the soil to determine a measure of phosphorus saturation, which provides an indication of how close the soil is to becoming saturated with phosphorus. In accordance with one embodiment, the measure of phosphorus saturation is determined by first determining a phosphorus storage capacity using the amount of phosphorus, aluminum and calcium in soil sample 102 as well as the pH of soil sample 102. In accordance with one embodiment, the phosphorus storage capacity is determined using the amount of phosphorus, aluminum and calcium in soil sample 102 and measures the degree to which soil phosphorus sorption sites have been filled.

At step 210, the phosphorus storage capacity is scaled by a saturation scaling module 120 executed by computing device 180. In one embodiment, this scaling is performed using a maximum phosphorus storage capacity and a minimum phosphorus storage capacity determined for the sample group of soil sample 102. Saturation scaling module 120 retrieves the maximum and minimum phosphorus storage capacities for the sample group from group maximum/minimum storage capacities 122. In accordance with one embodiment, the maximum and minimum phosphorus storage capacities are determined from phosphorus storage capacities of a collection of soil samples that fall within the sample group. In particular, the minimum storage capacity is calculated as the storage capacity of the soil sample marking the first quartile in the collection of soil samples minus 1.5 times the interquartile difference in storage capacities. The maximum storage capacity is calculated as the storage capacity of the soil sample marking the third quartile in the collection of soil samples of the group plus 1.5 times the interquartile difference in storage capacities. The scaled phosphorus storage capacity is then calculated as one hundred times the value of the storage capacity provided by saturation determination module 110 minus the minimum storage capacity for the group divided by the difference between the maximum storage capacity for the group minus the minimum storage capacity for the group. Thus, the scaled phosphorus storage capacity has a value between zero and one hundred, with larger values indicating more phosphorus sorption sites are filled in the soil. The resulting scaled phosphorus storage capacity provides the measure of phosphorus saturation.

At step 212, mineralization count module 112 executed by computing device 180 uses the biologic sequence reads produced by biologic tests 108 at step 306 of FIG. 3 to determine a count of the genes available in the soil sample that contribute to mineralization of phosphorus. Lists of genes involved in mineralization are obtained and cross validated from multiple sources, including the MetaCyc database, the Kyoto Encyclopedia of Genes and Genomes (KEGG) and SEED gene ontologies. Further data sources are used to obtain additional gene annotation sources or models, including the UniProt, Pfam, and InterPro databases. These databases generally represent known molecular biology across organisms as organized for varying purposes which are not commonly organized to represent element cycling, soils, or agriculture.

As a general note, several of the most relevant genes are known to be horizontally transferred among microbes (such that organism names or name hierarchies are not necessarily deterministic of gene count). The number of these gene copies may vary within a given organism name or group (taxonomy).

In various embodiments, mineralization count module 112 assigns the sequence reads to the corresponding genes in the reference databases in order to determine counts of each gene. Mineralization count module 112 normalizes gene counts using total reads or gene hits, rarefaction, normalization by single copy marker genes, or other transformations. Mineralization count module 112 may combine reads or normalized read counts of subunits of a gene. For example, the counts of subunits of a gene are averaged in one embodiment to produce a count for the gene.

Once gene counts are determined, mineralization count module 112 combines the gene counts into a function of the gene counts (e.g., an aggregate count) for phosphorus mineralization.

At step 214, the mineralization count produced by mineralization count module 112 is converted into a scaled mineralization score by a mineralization scaling module 124 executed by computing device 180. In one embodiment, this is performed by scaling the mineralization counts using a maximum phosphorus mineralization count and a minimum phosphorus mineralization count for the sample group of soil sample 102. Mineralization scaling module 124 retrieves the maximum and minimum phosphorus mineralization count for the sample group from group maximum/minimum mineralization counts 126. In accordance with one embodiment, the maximum and minimum mineralization counts are determined from mineralization counts of a collection of soil samples that fall within the sample group. In particular, the minimum mineralization count is calculated as the mineralization count of the soil sample marking the first quartile in the collection of soil samples for the group minus 1.5 times the interquartile difference in mineralization counts within the group. The maximum mineralization count is calculated as the mineralization count of the soil sample marking the third quartile in the collection of soil samples of the group plus 1.5 times the interquartile difference in mineralization counts within the group. The scaled mineralization count is then calculated as one hundred times the value of the mineralization count provided by mineralization count module 112 minus the minimum mineralization count for the group divided by the difference between the maximum mineralization count for the group minus the minimum mineralization count for the group. Thus, the scaled mineralization count has a value between zero and one hundred. This scaled mineralization count is also referred to as a mineralization function measure.

At step 216, solubilization count module 114 executed by computing device 180 uses the biologic sequence reads produced by biologic tests 108 at step 306 of FIG. 3 to determine a count of the genes available in the soil sample that contribute to solubilization of phosphorus. Lists of genes involved in solubilization are obtained and cross validated from multiple sources, including the MetaCyc database, the Kyoto Encyclopedia of Genes and Genomes (KEGG) and SEED gene ontologies. Further data sources are used to obtain additional gene annotation sources or models, including the UniProt, Pfam, and InterPro databases. These databases generally represent known molecular biology across organisms as organized for varying purposes which are not commonly organized to represent element cycling, soils, or agriculture.

As a general note, several of the most relevant genes are known to be horizontally transferred among microbes (such that organism names or name hierarchies are not necessarily deterministic of gene count). The number of these gene copies may vary within a given organism name or group (taxonomy).

In various embodiments, solubilization count module 114 assigns the sequence reads to the corresponding genes in the reference databases in order to determine counts of each gene. Solubilization count module 114 normalizes gene counts using total reads or gene hits, rarefaction, normalization by single copy marker genes, or other transformations. Solubilization count module 114 may combine reads or normalized read counts of subunits of a gene. For example, the counts of subunits of a gene are averaged in one embodiment to produce a count for the gene.

Once gene counts are determined, solubilization count module 114 combines the gene counts using a function (e.g., an aggregate count) to produce the phosphorus solubilization count.

At step 218, the solubilization count produced by solubilization count module 114 is converted into a scaled solubilization score by a solubilization scaling module 128 executed by computing device 180. In one embodiment, this is performed by scaling the solubilization counts using a maximum phosphorus solubilization count and a minimum phosphorus solubilization count for the sample group of soil sample 102. Solubilization scaling module 128 retrieves the maximum and minimum phosphorus solubilization count for the sample group from group maximum/minimum solubilization counts 130. In accordance with one embodiment, the maximum and minimum solubilization counts are determined from solubilization counts of a collection of soil samples that fall within the sample group. In particular, the minimum solubilization count is calculated as the solubilization count of the soil sample marking the first quartile in the collection of soil samples for the group minus 1.5 times the interquartile difference in solubilization counts within the group. The maximum solubilization count is calculated as the solubilization count of the soil sample marking the third quartile in the collection of soil samples of the group plus 1.5 times the interquartile difference in solubilization counts within the group. The scaled solubilization count is then calculated as one hundred times the value of the solubilization count provided by solubilization count module 114 minus the minimum solubilization count for the group divided by the difference between the maximum solubilization count for the group minus the minimum solubilization count for the group. Thus, the scaled solubilization count has a value between zero and one hundred. This scaled solubilization count is also referred to as a solubilization function measure.

At step 220, a biologic unification module 132 executed by computing device 180 combines the scaled mineralization count with the scaled solubilization count to provide a biologic score. In accordance with one embodiment, the biologic score is formed as a weighted sum of the scaled mineralization count and the scaled solubilization count. In accordance with one embodiment, the weights used to form the biologic score are selected so that the biologic score has the same range of values as the scaled phosphorus storage capacity. For example, when the scaled phosphorus storage capacity has a range between zero and one hundred and the scaled mineralization count and the scaled solubilization count each have a range between zero and one hundred, the weights are selected such that the sum of the weights is one thereby making the biologic score range between zero and one hundred. In one specific embodiment, the weights for the scaled mineralization count and the scaled solubilization count are the same. The biologic score is also referred to as a measure of biologic functions.

At step 222, the biologic score is combined with the scaled phosphorus storage capacity by biologic and saturation unification module 134 to form a Pcomposite score. In accordance with one embodiment, the Pcomposite score is the weighted sum of the biologic score and the scaled phosphorus storage capacity. The Pcomposite score is also referred to as a unified phosphorus measure.

At step 224, the scaled phosphorus storage capacity, the scaled mineralization count, the scaled solubilization count, the biologic score and the Pcomposite score are all stored in field scores 136 for the field that the soil sample was collected from. In accordance with some embodiments, each field is divided into multiple zones and the scaled phosphorus storage capacity, the scaled mineralization count, the scaled solubilization count, the biologic score and the Pcomposite score for each zone are determined from a respective soil sample collected from the zone. The scores for each zone are stored in field scores 136 for the zones' field.

Figure 4:
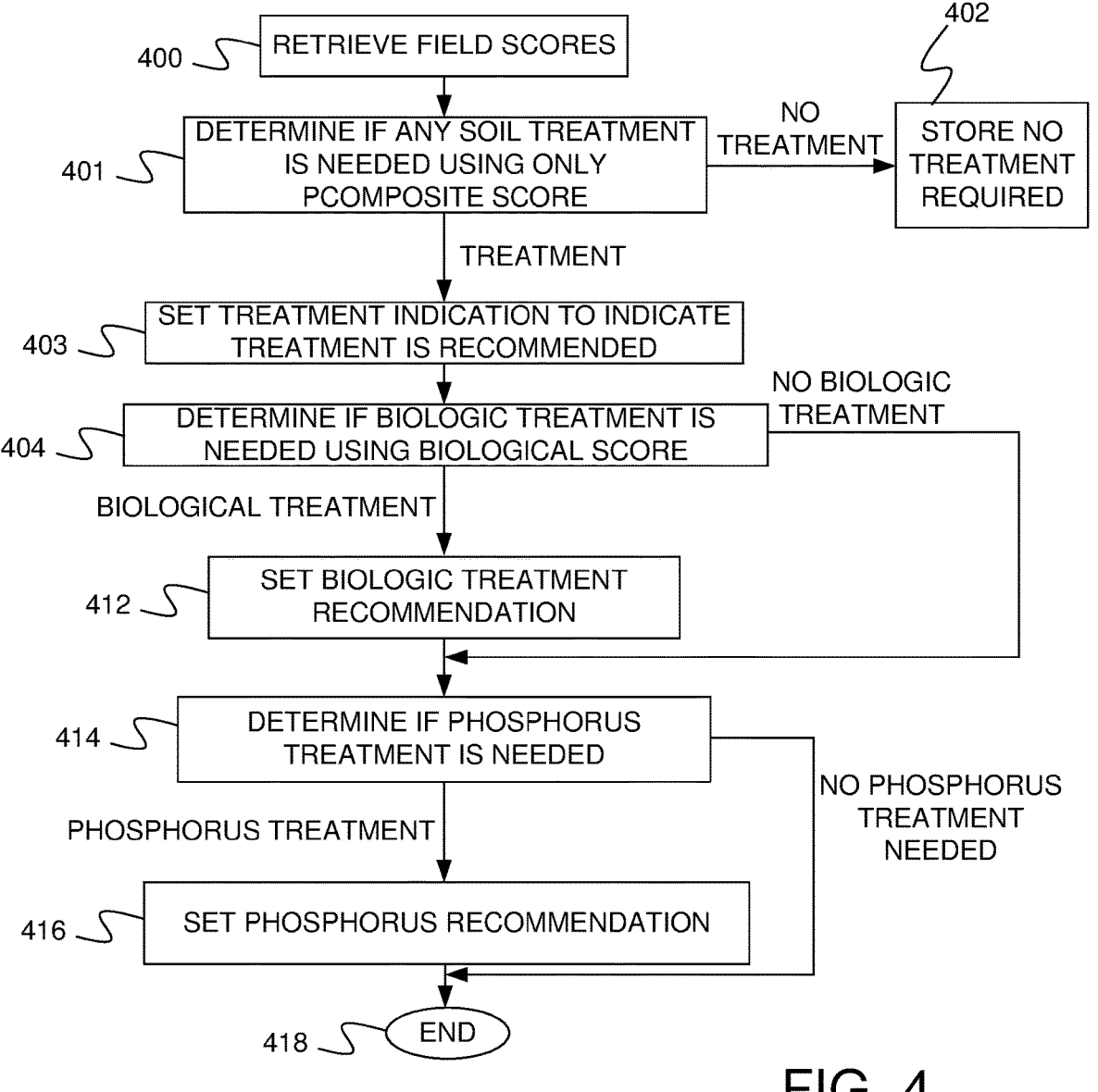
FIG. 4 is a flow diagram of a method setting treatment recommendations for a zone of a field.
Figure 5:
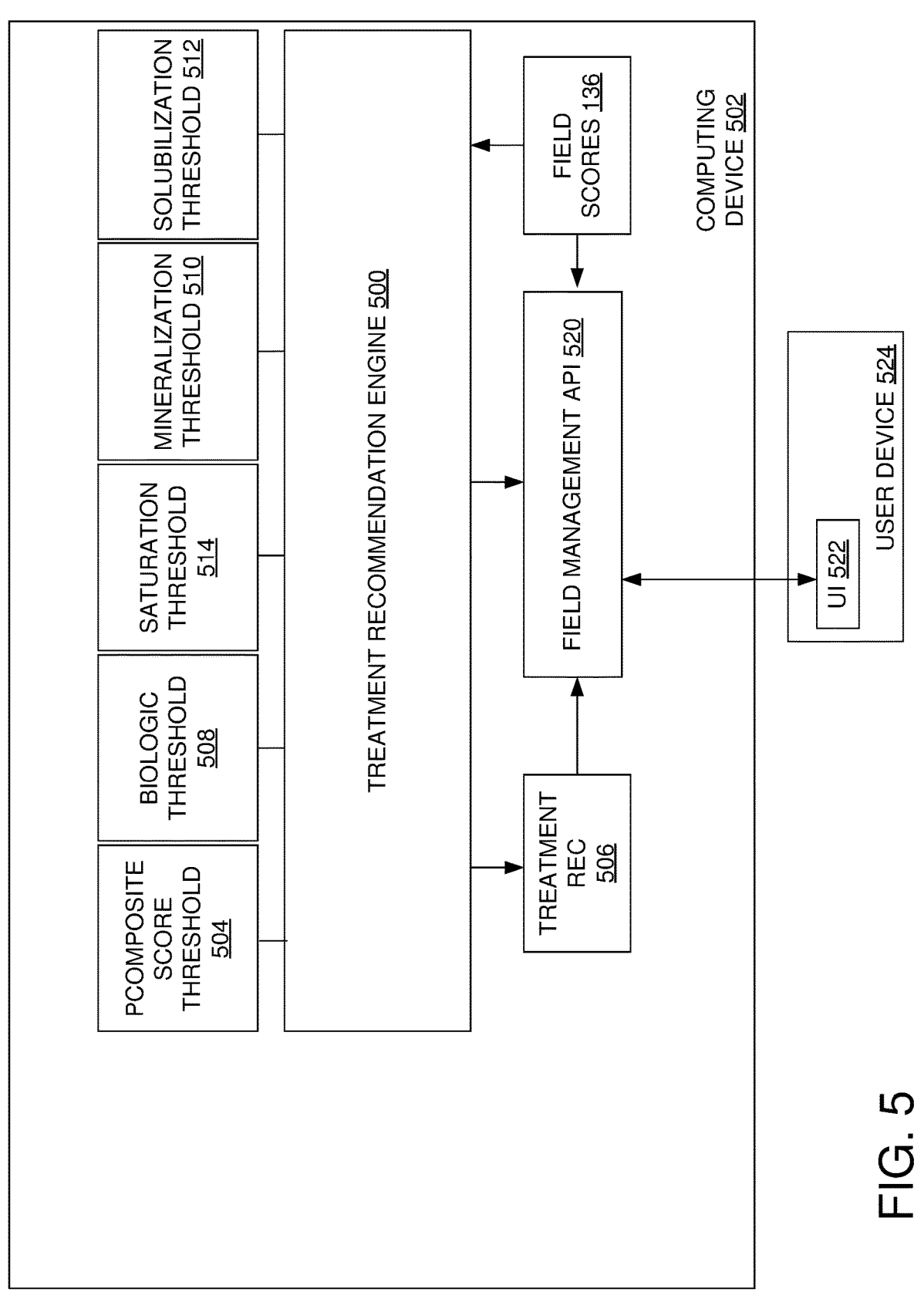
FIG. 5 is a block diagram showing elements used in the method of FIG. 4.

FIG. 4 provides a flow diagram of a method of identifying field treatments based on field scores 136. FIG. 5 provides a block diagram showing elements used in the method of FIG. 4. In the description below, the field treatments are discussed with reference to zones of a field. In embodiments where a field is not divided into zones, the entire field would be considered a single zone.

In step 400, a treatment recommendation engine 500 executed by a processor on a computing device 502 retrieves the field scores 136 for a zone. At step 401, recommendation engine 500 determines if any soil treatment is needed for the zone using the Pcomposite score for the zone. In one embodiment, this involves comparing the Pcomposite score to a Pcomposite score threshold 504. Since the Pcomposite score is a combination of the scaled phosphorus storage capacity and the biologic score, a Pcomposite score that is below the threshold indicates that the zone has little to no saturation for additional phosphorus while simultaneously having a low potential for improving the phosphorus biologics in the zone. Thus, if the Pcomposite score is above the threshold, no treatment is required and no other scores need to be evaluated. At step 402, an indication that no treatment is needed for this zone is stored in treatment recommendations 506 to be used later for generating user interfaces that quickly and easily inform a user of which zones need treatment.

If the Pcomposite score is below the threshold, the zone would benefit from some treatment. As such, at step 403, an indication that treatment is recommended is set for the zone in treatment recommendations 506. However, it is not clear from the Pcomposite score itself whether a phosphorus treatment or a biologic-based treatment is needed. After step 403, the biologic score is examined at step 404 to determine if a biologic-based treatment is needed. In accordance with one embodiment, the biologic score is compared to a biologic threshold 508. If the biologic score exceeds the threshold, no biologic-based treatment is recommended and the process continues at step 414. If the biologic score exceeds biologic threshold 508, a biologic treatment recommendation is set at step 412.

After step 412, or if no biologic treatment is needed at step 404, treatment recommendation engine 500 determines if a phosphorus treatment is needed at step 414. In accordance with one embodiment, treatment recommendation engine 500 makes this determination by comparing the scaled storage capacity for the zone to a saturation threshold 514. If the scaled storage capacity exceeds the threshold at step 414, no phosphorus treatment should be applied because the soil is incapable of storing any further phosphorus. If the scaled storage capacity does not exceed the threshold, treatment recommendation engine 500 stores a phosphorus treatment recommendation in treatment recommendations 506 at step 416. In accordance with one embodiment, the phosphorus treatment recommendation is based in part on the difference between the scaled storage capacity and saturation threshold 514.

After step 416 or if no phosphorus treatment is needed at step 414, the process of FIG. 4 ends at step 418.

As shown above, the scaled mineralization count, the scaled solubilization count and the scaled storage capacity provide more accurate treatment recommendations from the precision farming system. In particular, the scaled mineralization count and the scaled solubilization count provide a more accurate representation of the biological functions that are attainable for the soil in the zone and thus when a biologic treatment is recommended it is more likely to result in an improvement in yield of the zone. Similarly, the scaled storage capacity provides a more accurate representation of the amount of phosphorus that can be added to the field without saturation and thus when a phosphorus treatment is recommended based on the scaled storage capacity it is more likely to result in an improvement in the yield of the zone.

A field management API 520 is used to access measured characteristics of zones and recommendations for treatments in zones. Although field management API 520 is shown executing on computing device 502, in other embodiments, field management API 520 is executed on a separate server or on a user device.

In accordance with one embodiment, upon a request from user device 524, field management API 520 retrieves one or more field maps that show fields associated with a current user of user device 524. Each field map includes a graphical depiction of one or more fields with lines representing the boundaries of each field and in some embodiments, additional lines depicting zones within each field. After retrieving a map, field management API 520 sets fill colors of the zones of each field to depict one or more measured characteristics of the zones.

Figure 6:
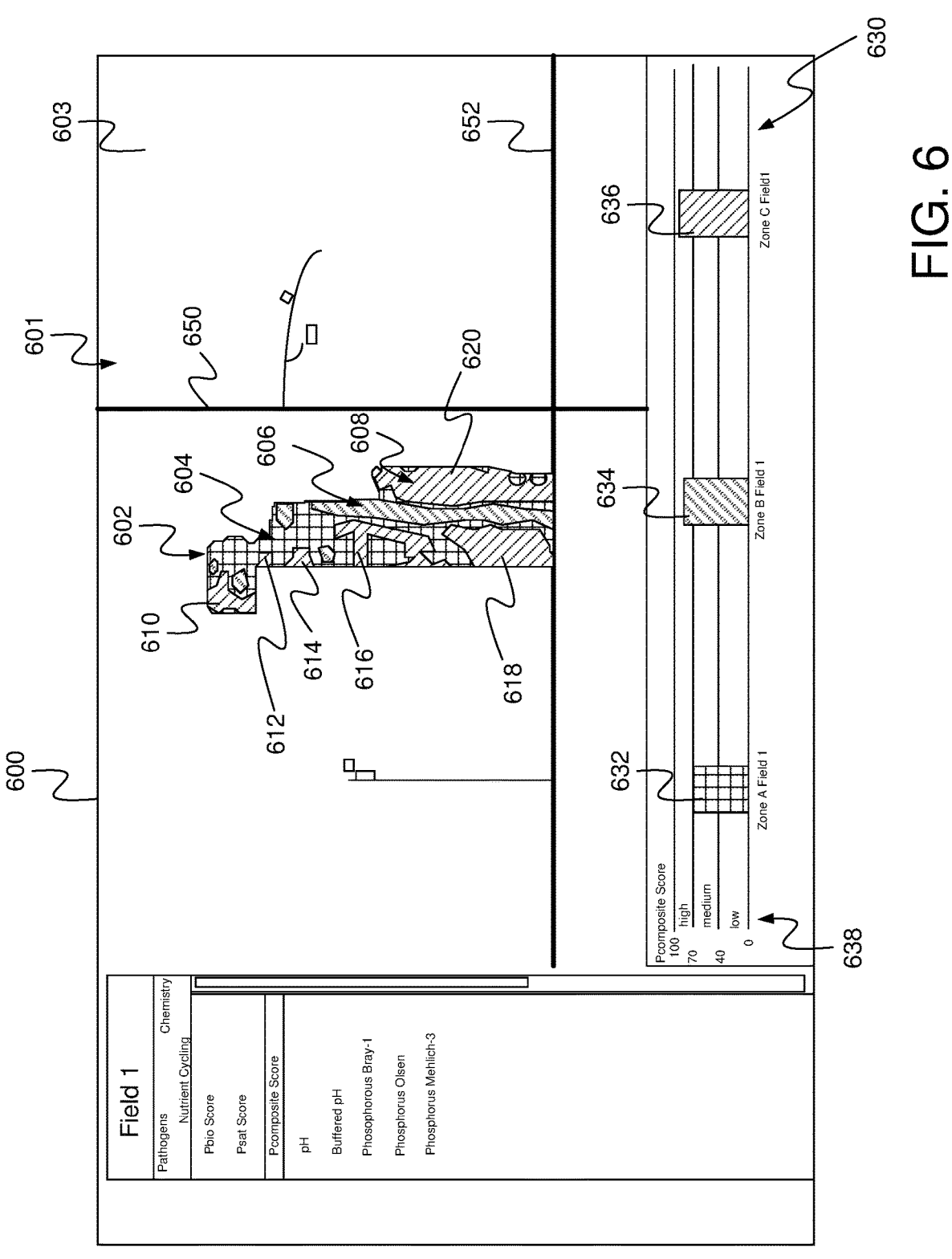
FIG. 6 is an example user interface depicting unified phosphorus scores for zones of a field on a map.

FIG. 6 provides an example user interface 600 showing a map 601 containing a field 602 showing Pcomposite scores for zones in the field. Map 601 includes a satellite view 603 of a geographic area surrounding field 602 including, for example, roads 650 and 652. Field 602 is depicted as being divided into three zones 604, 606 and 608, which are each shown in a different color on user interface 600. (In FIG. 6, the different colors are represented using different hashing). An individual zone is not limited to being within a single closed zone boundary but instead can be constructed of multiple areas each defined by a separate respective zone boundary. For example, zone 608 covers noncontiguous areas 610, 612, 614, 616, 618, 620 and 622. In accordance with one embodiment, each zone is formed of areas in the field that have similar characteristics.

User interface 600 also includes bar chart 630 that shows bars 632, 634 and 636 representing the respective Pcomposite Scores for zones 604, 606, and 608. Each bar has the same coloring as the corresponding zone shown in map 601. Bar chart 630 also includes designations 638 indicating whether the Pcomposite Score for the zone is "high", "medium", or "low". Zones with Pcomposite Scores that are in the "high" range require less phosphorus or no biologic treatment. Zones with Pcomposite Scores in the "low" range would definitely be improved with one or both of a phosphorus treatment and/or phosphorus liberating product application and a biologic treatment.

In bar chart 630 all of zones 604, 606 and 608 are shown as having a Pcomposite Score in the "high" range. This indicates that less phosphorus is needed since the combination of phosphorus levels and biologic levels makes enough phosphorus available to the plants in each zone. Thus, by looking at just user interface 600, a farmer is able to determine that no phosphorus or biologic remediations are needed for any of the zones of field 602.

Figure 7:
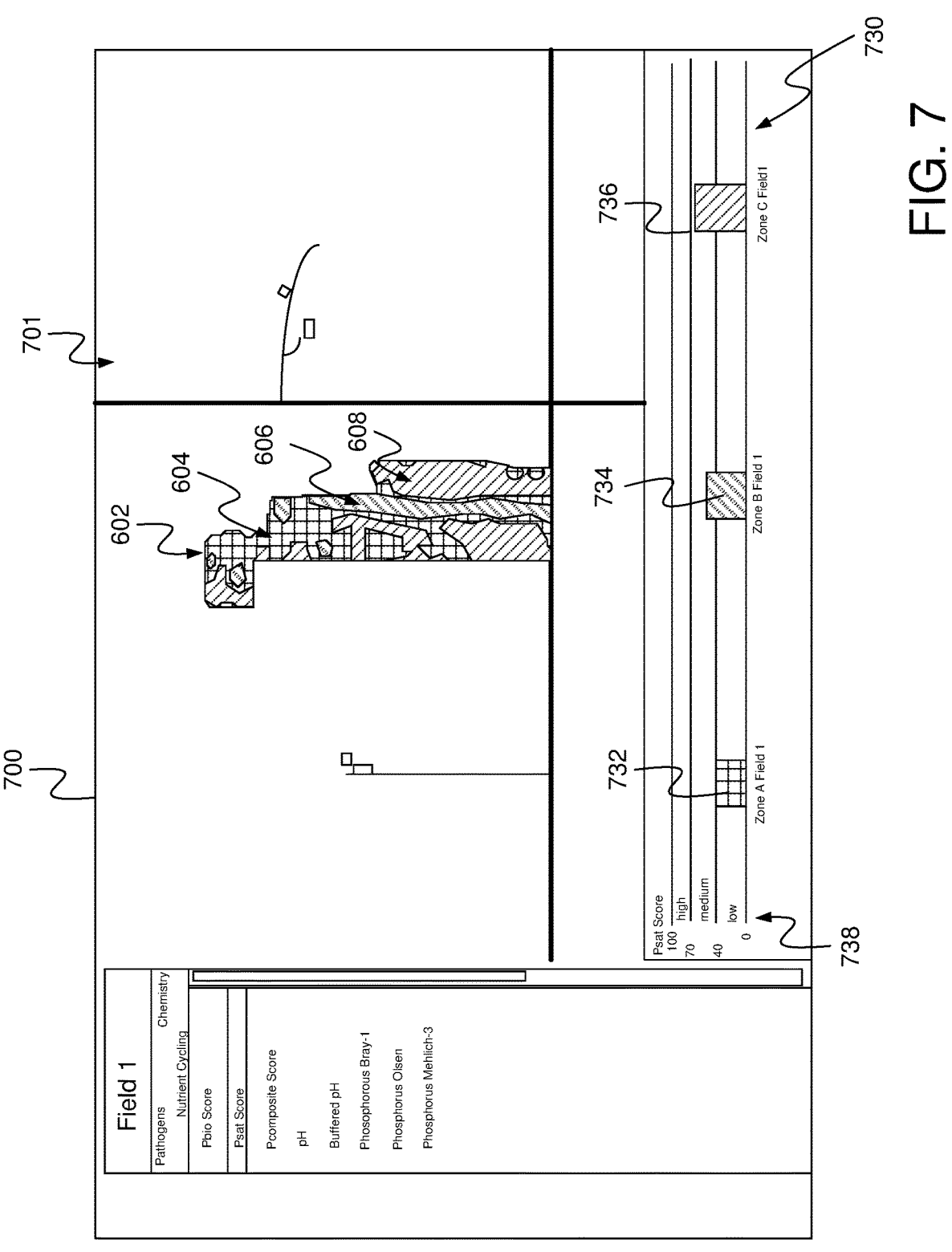
FIG. 7 is an example user interface depicting scaled phosphorus storage capacities for zones of a field on a map.
Figure 8:
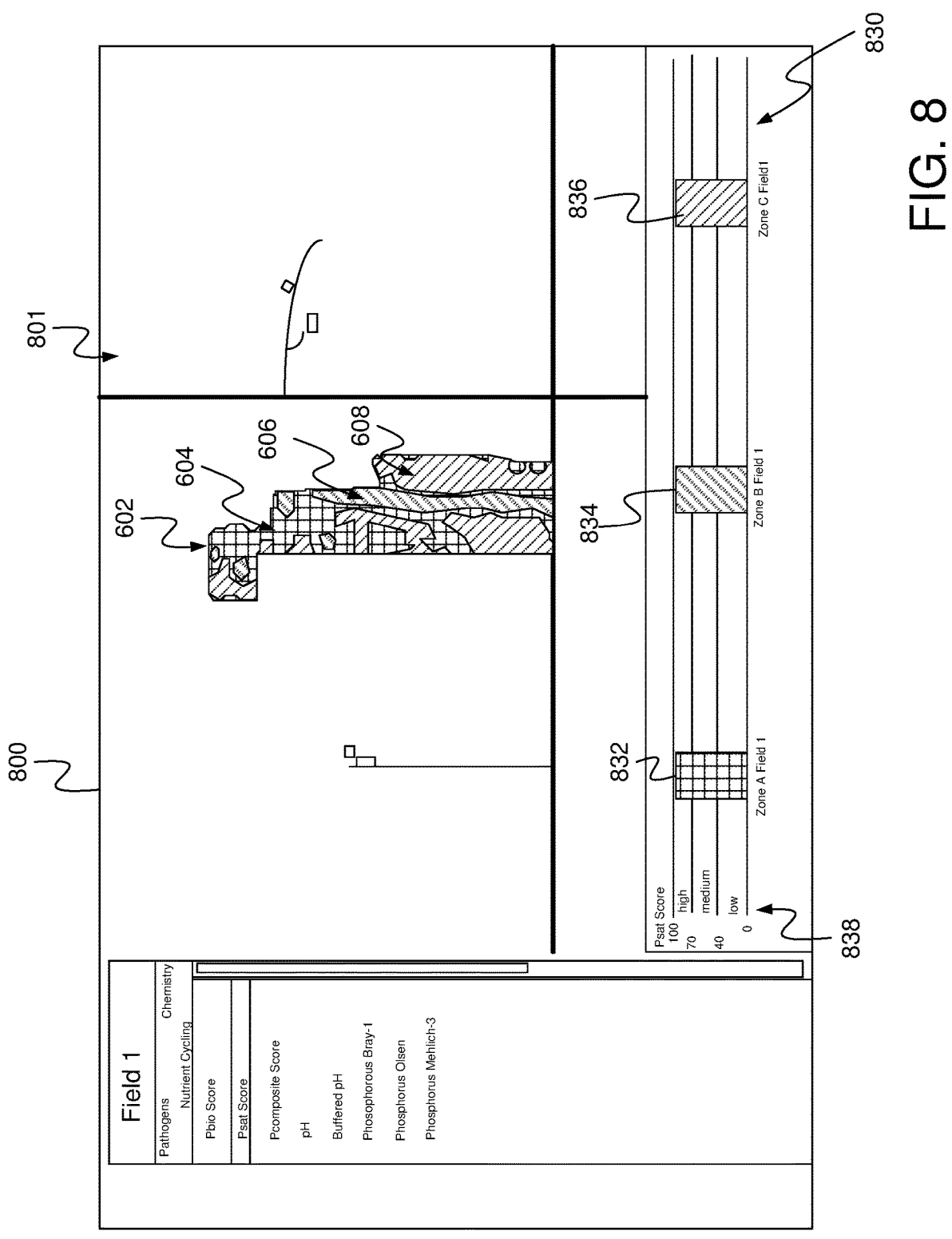
FIG. 8 is an example user interface depicting biologic scores for zones of a field on a map.

Note that although the Pcomposite score of the zones of field 602 indicate that no phosphorus or biologic treatment is needed for any of the zones, the zones can still be deficient in either phosphorus or biologics. For example, this can occur when a zone has a low level of phosphorus but a high level of biologic functions. FIGS. 7 and 8 provide user interfaces 700 and 800 showing scaled phosphorus scores and biologic scores for field 602 that provide an example of such a zone.

User interface 700 of FIG. 7 shows a map 701 that includes field 602 and depicts scaled phosphorus storage capacities for zones 604, 606 and 608. User interface 800 of FIG. 8 shows a map 801 that includes field 602 and depicts biologic scores for zones 604, 606 and 608. In FIG. 7, a bar chart 730 includes respective bars 732, 734 and 736 for zones 604, 606 and 608 depicting the scaled phosphorus scores for each zone. Each bar has the same coloring as the corresponding zone shown in map 701. Bar chart 730 also includes designations 738 indicating whether the scaled phosphorus storage capacity for the zone is "high", "medium", or "low". Zones with scaled phosphorus storage capacities that are in the "high" range do not require any phosphorus and in fact should not have phosphorus added to them because it is likely to run off. Zones with scaled phosphorus storage capacities that are in the "medium" range can accept some additional phosphorus. Zones with scaled phosphorus scores in the "low" range can accept a large amount of additional phosphorus.

In FIG. 8, a bar chart 830 includes respective bars 832, 834 and 836 for zones 604, 606 and 608 depicting the biologic scores for each zone. Each bar has the same coloring as the corresponding zone shown in map 801. Bar chart 830 also includes designations 838 indicating whether the biologic score for the zone is "high", "medium", or "low". Zones with biologic scores that are in the "high" range have a large amount of biologic function, zones with biologic scores that are in the "medium" range have an intermediate amount of biologic function, and zones with biologic scores in the "low" range have a small amount of biologic function.

As shown by bar 732 of FIG. 7, zone 604 has a low amount of phosphorus. Looking at user interface 701 alone, a farmer may incorrectly conclude that phosphorus should be applied to zone 604. This is incorrect because bar 832 of FIG. 8 indicates that zone 604 has a very high biologic function. However, it is difficult for a farmer to determine that phosphorus does not need to be applied to zone 604 using user interfaces 701 and 801, because the farmer would have to compare depictions of the zone in two different user interfaces and make a judgement about whether the biologic score depicted in user interface 801 indicates a sufficient amount of biologic function to overcome the low phosphorus depicted in user interface 701.

The embodiments shown in FIGS. 7 and 8 quickly convey to a farmer whether a treatment is required for a zone of a field. In particular, since the values depicted are scaled for groups of soil samples, they provide a better indication of the levels of phosphorus and phosphorus functions that are attainable in each zone and thus better convey to the farmer whether a treatment would improve the yield of the zone.

Figure 9:
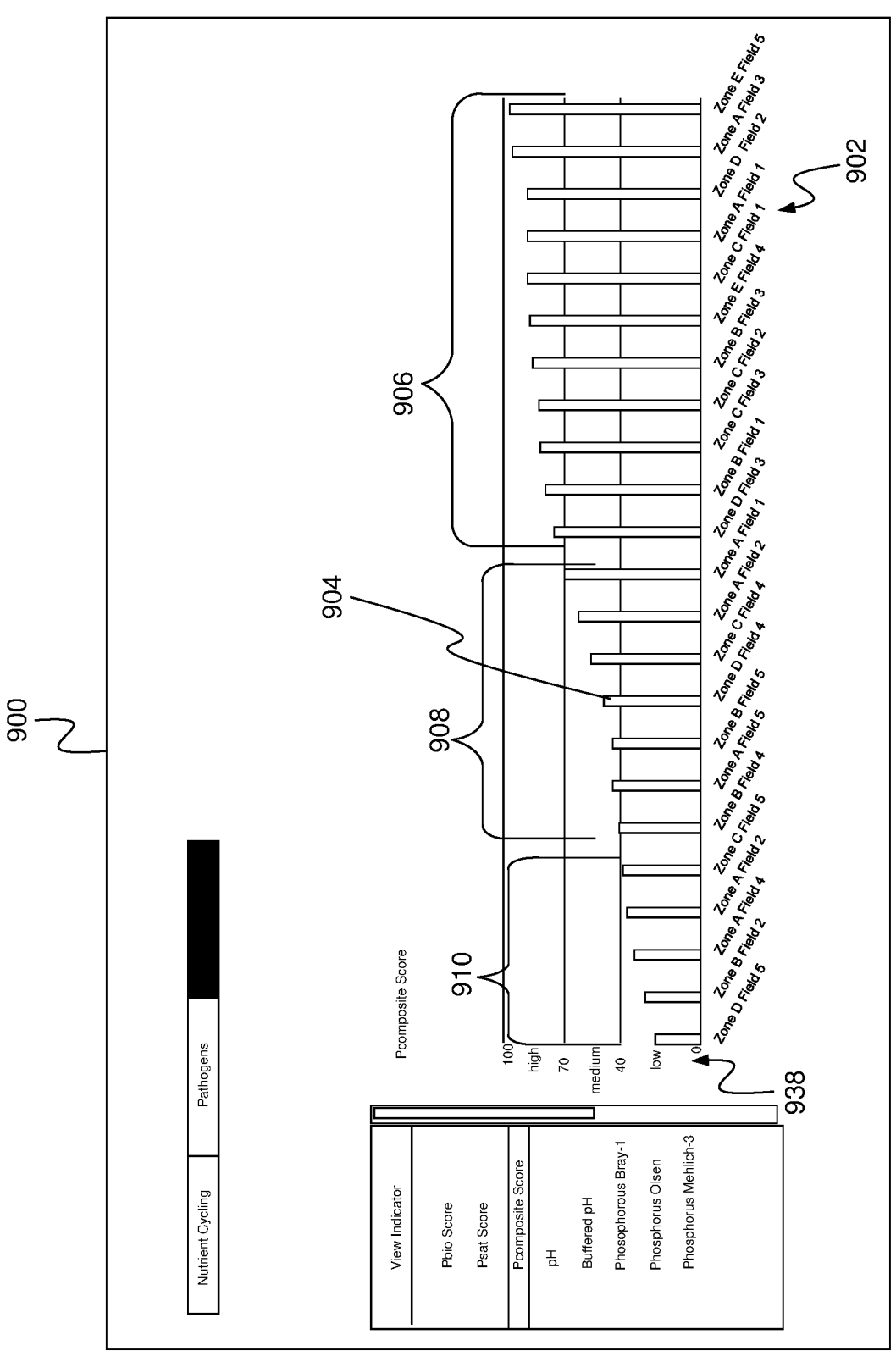
FIG. 9 is an example of a user interface depicting unified phosphorus scores for zones across a collection of fields.

In other embodiments, the Pcomposite scores for a collection of fields are shown together in a single user interface. FIG. 9 provides an example of such a user interface 900, which provides a bar chart 902 of Pcomposite scores for each zone of a collection of fields. In user interface 900, a separate bar is provided for each zone of the collection of fields. For example, bar 904 is provided for zone D of Field 4. In addition, designations 938 indicate whether the Pcomposite Scores for the zones are "high", "medium", or "low". Zones with Pcomposite Scores that are in the "high" range do not require any phosphorus or biologic treatment. Zones with Pcomposite Scores that are in the "medium" range could be improved with one or both of a phosphorus or biologic treatment. Zones with Pcomposite Scores in the "low" range would definitely be improved with one or both of a phosphorus treatment and a biologic treatment. In FIG. 9, zones 906 are shown to have Pcomposite scores in the high range, zones 908 are shown to have Pcomposite scores in the medium range, and zones 910 are shown to have Pcomposite scores in the low range.

Using FIG. 9, a farmer can quickly determine that zones 906 do not require any treatment to make more phosphorus available to plants in those zones. For zones 908 and 910, the farmer can use field map user interfaces, like those of FIGS. 7 and 8, to determine whether the zone is lacking in phosphorus, biologic function or both.

Figure 10:
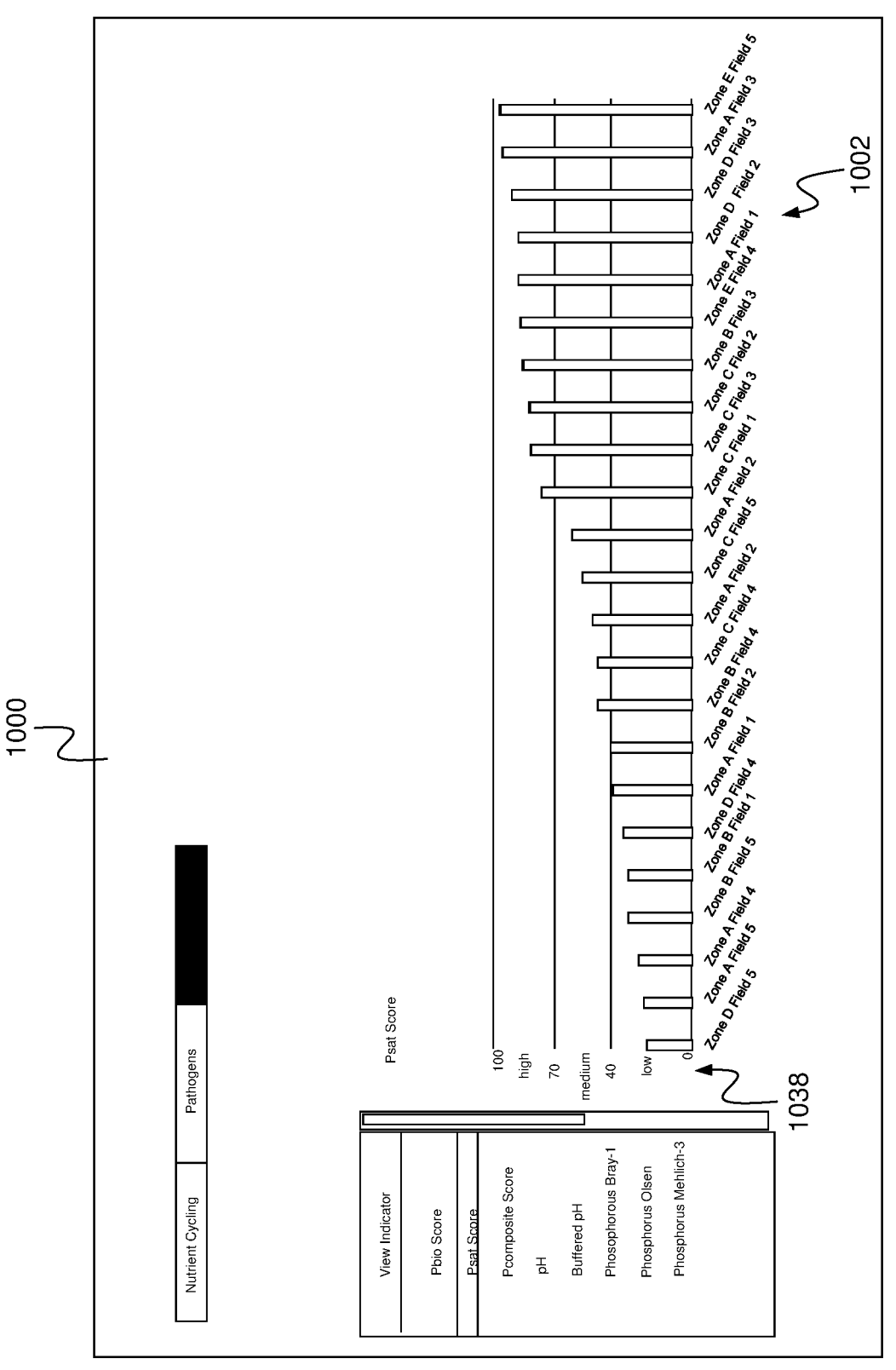
FIG. 10 is an example of a user interface depicting scaled phosphorus storage capacities for zones across a collection of fields.
Figure 11:
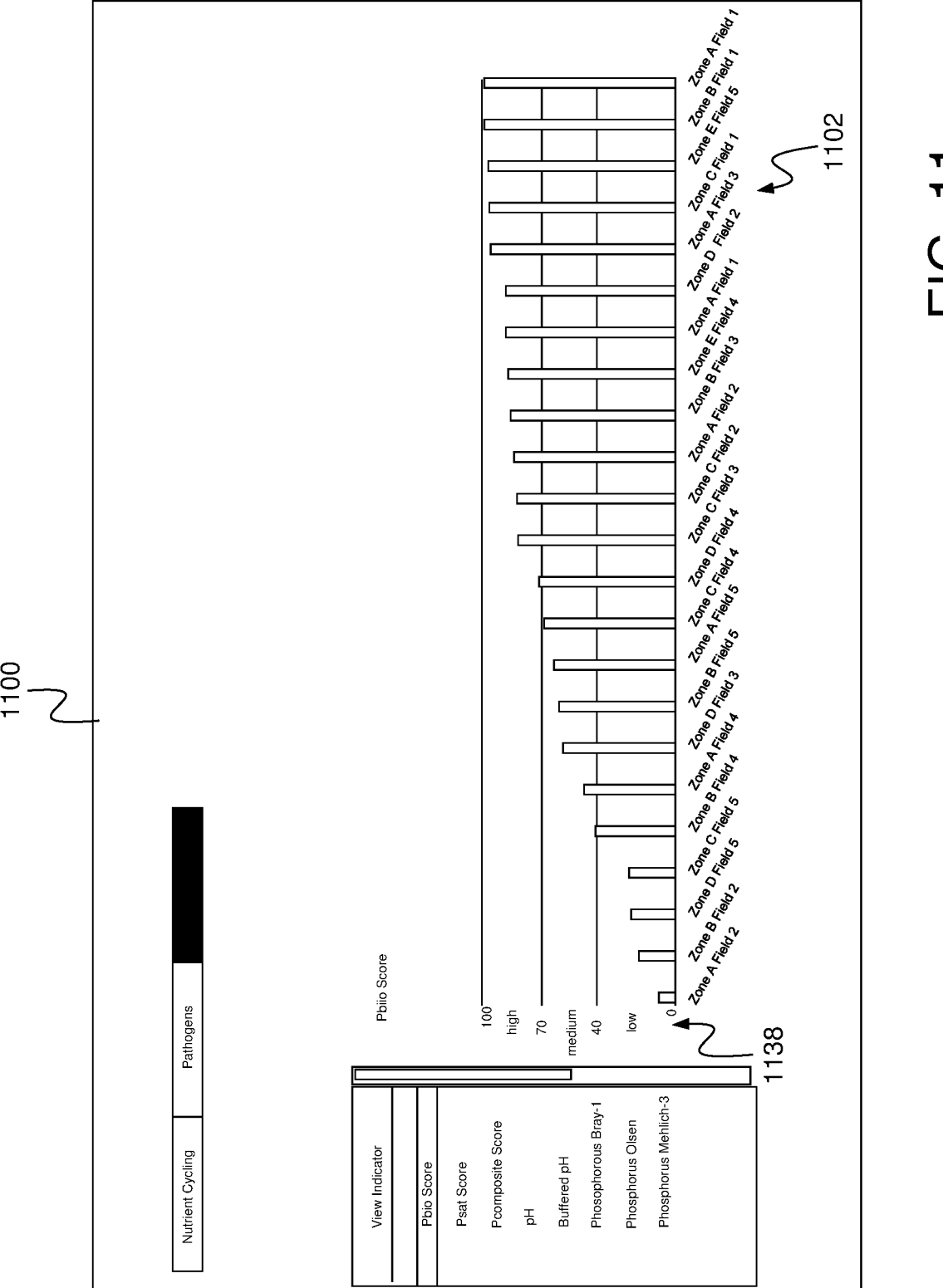
FIG. 11 is an example of a user interface depicting biologic scores for zones across a collection of fields.

In further embodiments, field management API 520 also provides user interfaces 1000 and 1100 of FIGS. 10 and 11, respectively, that provide bar charts 1002 and 1102 depicting scaled phosphorus storage capacities and biologic scores for the collection of zones shown in FIG. 9. Bar chart 1002 includes designations 1038 indicating whether the scaled phosphorus storage capacity for the zone is "high", "medium", or "low". Zones with scaled phosphorus storage capacities that are in the "high" range do not require any phosphorus and in fact should not have phosphorus added to them because it is likely to run off. Zones with scaled phosphorus storage capacities that are in the "medium" range can accept some additional phosphorus. Zones with scaled phosphorus scores in the "low" range can accept a large amount of additional phosphorus. Bar chart 1102 includes designations 1138 indicating whether the biologic score for the zone is "high", "medium", or "low". Zones with biologic scores that are in the "high" range have a large amount of biologic function, zones with biologic scores that are in the "medium" range have an intermediate amount of biologic function, and zones with biologic scores in the "low" range have a small amount of biologic function.

Figure 12:
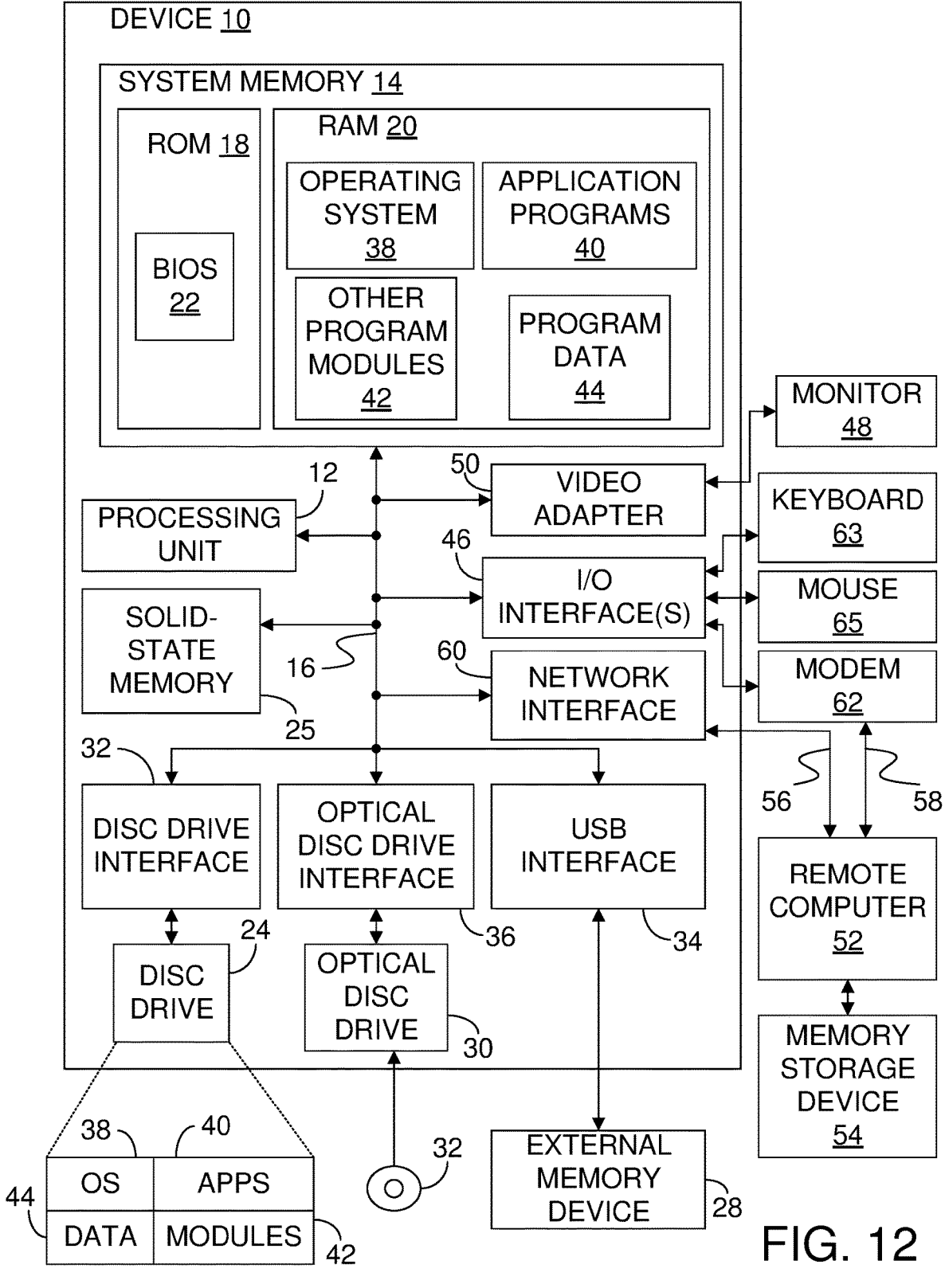
FIG. 12 provides a block diagram of a computing device used to implement the various embodiments.

FIG. 12 provides an example of a computing device 10 that can be used to implement each of computing devices 180, 502 and 524 above. Computing device 10 includes a processing unit 12, a system memory 14 and a system bus 16 that couples the system memory 14 to the processing unit 12. System memory 14 includes read only memory (ROM) 18 and random-access memory (RAM) 20. A basic input/output system 22 (BIOS), containing the basic routines that help to transfer information between elements within the computing device 10, is stored in ROM 18. Computer-executable instructions that are to be executed by processing unit 12 may be stored in random access memory 20 before being executed.

Computing device 10 further includes an optional hard disc drive 24, an optional external memory device 28, and an optional optical disc drive 30. External memory device 28 can include an external disc drive or solid-state memory that may be attached to computing device 10 through an interface such as Universal Serial Bus interface 34, which is connected to system bus 16. Optical disc drive 30 can illustratively be utilized for reading data from (or writing data to) optical media, such as a CD-ROM disc 32. Hard disc drive 24 and optical disc drive 30 are connected to the system bus 16 by a hard disc drive interface 32 and an optical disc drive interface 36, respectively. The drives and external memory devices and their associated computer-readable media provide nonvolatile storage media for the computing device 10 on which computer-executable instructions and computer-readable data structures may be stored. Other types of media that are readable by a computer may also be used in the exemplary operation environment.

A number of program modules may be stored in the drives and RAM 20, including an operating system 38, one or more application programs 40, other program modules 42 and program data 44. In particular, application programs 40 can include programs for implementing the modules, engines and APIs discussed above. Program data 44 may include any data used by the systems and methods discussed above.

Processing unit 12, also referred to as a processor, executes programs in system memory 14 and solid-state memory 25 to perform the methods described above.

Input devices including a keyboard 63 and a mouse 65 are optionally connected to system bus 16 through an Input/Output interface 46 that is coupled to system bus 16. Monitor or display 48 is connected to the system bus 16 through a video adapter 50 and provides graphical images to users. Other peripheral output devices (e.g., speakers or printers) could also be included but have not been illustrated. In accordance with some embodiments, monitor 48 comprises a touch screen that both displays input and provides locations on the screen where the user is contacting the screen.

The computing device 10 may operate in a network environment utilizing connections to one or more remote computers, such as a remote computer 52. The remote computer 52 may be a server, a router, a peer device, or other common network node. Remote computer 52 may include many or all of the features and elements described in relation to computing device 10, although only a memory storage device 54 has been illustrated in FIG. 12. The network connections depicted in FIG. 12 include a local area network (LAN) 56 and a wide area network (WAN) 58. Such network environments are commonplace in the art.

The computing device 10 is connected to the LAN 56 through a network interface 60. The computing device 10 is also connected to WAN 58 and includes a modem 62 for establishing communications over the WAN 58. The modem 62, which may be internal or external, is connected to the system bus 16 via the I/O interface 46.

In a networked environment, program modules depicted relative to the computing device 10, or portions thereof, may be stored in the remote memory storage device 54. For example, application programs may be stored utilizing memory storage device 54. In addition, data associated with an application program may illustratively be stored within memory storage device 54. It will be appreciated that the network connections shown in FIG. 12 are exemplary and other means for establishing a communications link between the computers, such as a wireless interface communications link, may be used.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A method of indicating a characteristic of a soil sample of a field, the method comprising:

measuring a co-factor in the soil sample;

using the co-factor to place the soil sample in a soil sample group;

measuring the characteristic of the soil sample, the characteristic of the soil sample comprising a phosphorus storage capacity of the soil sample, and the phosphorus storage capacity of the soil sample is determined using the amount of phosphorus, aluminum, and calcium in the soil sample;

scaling the measured characteristic based on the soil sample group the soil sample is placed into to form a scaled measure;

displaying the scaled measure to better represent the characteristic of the soil sample relative to soil samples of the soil sample group.

2. The method of claim 1 wherein the co-factor comprises a pH of the soil sample.

3. The method of claim 1 wherein the co-factor comprises a phosphorus content of the soil sample.

4. The method of claim 1 wherein the co-factor comprises a plurality of co-factors and wherein the plurality of co-factors are used to select the soil sample group.

5. The method of claim 1 wherein the characteristic of the soil sample further comprises a biologic function of the soil sample.

6. The method of claim 1, further comprising determining a biologic measure of the soil sample relative to soil samples in the soil sample group.

7. The method of claim 6, wherein the biologic measure comprises a mineralization function measure.

8. The method of claim 6, wherein the biologic measure comprises a solubilization function measure.

9. The method of claim 6, wherein the biologic measure comprises a combination of a solubilization function measure and a mineralization function measure.

10. A method comprising:

using a pH of a soil sample to select a group of soil samples;

measuring a characteristic of the soil sample to produce a measured value, the characteristic of the soil sample comprising a phosphorus storage capacity of the soil sample, and the phosphorus storage capacity of the soil sample is determined using the amount of phosphorus, aluminum, and calcium in the soil sample;

scaling the measured value based on measured values determined for soil samples in the group of soil samples to form a scaled value;

displaying the scaled value instead of the measured value so as to improve a precision farming system.

11. The method of claim 10 wherein the characteristic further comprises a phosphorus mineralization function.

12. The method of claim 10 wherein the characteristic further comprises a phosphorus solubilization function.

\* \* \* \* \*